(12) United States Patent
Grodsky (10) Patent No.: US 7,837,930 B2
(45) Date of Patent: Nov. 23, 2010

(54) FRAGRANCE DIFFUSER KIT AND METHOD

(75) Inventor: Mark D. Grodsky, Phoenix, AZ (US)

(73) Assignee: Rich Brands LLC, Phoenix, AZ (US)

( * ) Notice: Subject to any disclaimer, the term of this patent is extended or adjusted under 35 U.S.C. 154(b) by 714 days.

(21) Appl. No.: 11/750,920

(22) Filed: May 18, 2007

(65) Prior Publication Data
US 2008/0286143 A1 Nov. 20, 2008

(51) Int. Cl.
*A61L 9/00* (2006.01)
*A62B 7/08* (2006.01)
*A24F 25/00* (2006.01)
*B65B 1/04* (2006.01)
*A01M 13/00* (2006.01)
*A01M 7/00* (2006.01)

(52) U.S. Cl. .................. 422/5; 422/1; 422/123; 422/126; 422/306; 239/44; 239/302; 141/2; 141/18; 43/1; 43/124; 43/125; 43/900

(58) Field of Classification Search .......... 422/1, 422/5, 123, 126, 306; 239/44, 302; 141/2, 141/18; 43/1, 124–125, 900
See application file for complete search history.

(56) References Cited

U.S. PATENT DOCUMENTS

| | | | |
|---|---|---|---|
| 4,739,928 A * | 4/1988 | O'Neil | ............ 239/45 |
| 4,762,275 A | 8/1988 | Herbert et al. | |
| 5,081,104 A | 1/1992 | Orson, Sr. | |
| 5,437,410 A | 8/1995 | Babasade | |
| 6,413,476 B1 | 7/2002 | Barnhart | |
| 6,581,915 B2 | 6/2003 | Bartsch et al. | |
| 6,619,560 B1 | 9/2003 | Chun | |
| 6,658,604 B1 | 12/2003 | Corbin et al. | |
| 7,007,863 B2 | 3/2006 | Kotary et al. | |
| 7,017,829 B2 | 3/2006 | Martens, III et al. | |

(Continued)

OTHER PUBLICATIONS http://cgi.ebay.com/modele-depose-fragrance-decanter_W0QQitem Z7201, Aug. 16, 2007.

(Continued)

*Primary Examiner*—Jill Warden
*Assistant Examiner*—Monzer R. Chorbaji
(74) *Attorney, Agent, or Firm*—Townsend and Townsend and Crew LLP (57) ABSTRACT

A fragrance diffuser kit is provided comprising a decanter, a fragrance refill set, a removable snuffer cap and a removable decorative vented lid. The decanter may be selected from a plurality of unique and decorative designs that are suitable for prominent display as a piece of home décor. The fragrance refill set comprises a bottle of high-quality fragrance composition for filling the decanter and a replacement wick, whereby the user may select and change the fragrance emitted by the fragrance diffuser. The decanter incorporates a wick holder having a top opening that communicates with a top opening in the decanter body so that a wick from the fragrance refill set may be inserted and held in a position to absorb and emit the fragrance composition contained in the decanter. The snuffer cap may be used to stop the emission of the fragrance composition and the vented lid may be used to hide the wick and snuffer cap, if present.

9 Claims, 7 Drawing Sheets

U.S. PATENT DOCUMENTS

| | | |
|---|---|---|
| 7,025,283 B2 | 4/2006 | Torres |
| 7,157,057 B2 | 1/2007 | Gohil |
| 7,223,361 B2 * | 5/2007 | Kvietok et al. ................ 422/4 |
| 2004/0118477 A1 * | 6/2004 | Desmond ................ 141/18 |

OTHER PUBLICATIONS http://cgi.ebay.com/avon-decorative-france-decanter_W0QQitemZ280143144573Q, Aug. 16, 2007.

* cited by examiner

FRAGRANCE DIFFUSER KIT AND METHOD

BACKGROUND OF THE INVENTION

This invention relates to aromatic substance diffusers and in particular to passive or "static" fragrance diffusers. Specifically, this invention relates to a kit for providing a fragrance diffuser and a method for using it.

Fragrance diffusers comprising a reservoir for holding a fragrance composition and an absorbent wick for drawing the fragrance composition via capillary action to a surface from which the fragrance can evaporate into the surrounding environment are known. The fragrance composition absorbed in the wick is exposed to normal air currents within an environment to dispense the fragrance in vapors throughout the area without resorting to fans, jet sprays, heating devices, and so on.

Typically these fragrance diffuser products are designed to be thrown away when the fragrance composition has been expended. As such, the products are manufactured of inexpensive disposable materials and do not have the esthetically pleasing appearance and high quality that would allow them to be prominently displayed as part of the permanent décor of a home. In addition, such prior art fragrance diffusers are usually capable of dispensing only one fragrance and cannot be refilled. If a different fragrance is desired for a room, the entire diffuser has to be replaced with another one. Typically the choices of fragrance are limited and the fragrance composition does not have the unique and complex characteristics of a fine cosmetic perfume.

BRIEF SUMMARY OF THE INVENTION

The present invention provides a fragrance diffuser kit useful for introducing a variety of sophisticated fragrances into a home environment. In one embodiment, the fragrance diffuser kit comprises a decanter, a fragrance refill set, a removable snuffer cap and a removable decorative vented lid. The decanter may be selected from a plurality of unique and decorative designs that are suitable for prominent display as a piece of home décor. The fragrance refill set allows the user to select and change the fragrance emitted by the fragrance diffuser.

In one embodiment, the decanter has a distinctive decorative hollow body with an annular top opening, and a wick holder fixedly secured to the hollow body. The wick holder has an annular top opening that communicates with the top opening of the decanter body. The fragrance refill set may contain a bottle of a volatile liquid fragrance composition for filling the decanter body and a rod-shaped wick adapted to be removably held by the wick holder of the decanter so that a bottom portion of the wick is immersed in fragrance composition contained in the decanter body and a top portion extends above the wick holder a distance sufficient to allow fragrance composition absorbed in the wick to evaporate therefrom. In one embodiment, the removable snuffer cap is adapted to be installed on the wick holder over the top portion of the wick. The removable decorative vented lid is adapted to cover the wick holder, the top portion of the wick and the snuffer cap, when present, and rest on the decanter body to add to the ornamental design of the diffuser. When the top portion of the wick is covered only by the vented lid, vapors of the fragrance composition are released through the vents and into the environment to depart a distinctive fragrance to the surroundings. When the top portion of the wick is covered by the snuffer cap, the release of fragrance is prevented. The decorative vented lid may be replaced over the wick holder to hide the snuffer cap.

In one embodiment, the decanter body has a protruding lip around the circumference of the top opening, and the wick holder comprises three vertically disposed concentric cylindrical sections; a top section, a middle section and a bottom section. The inner circumferences of the top and middle sections define a closed hollow passageway connecting the top opening in the decanter body to a top opening in the wick holder. The inner circumference of the bottom section engages the vertically protruding lip of the decanter body to secure the wick holder to the decanter body. The outer circumference of the middle section is larger than the outer circumference of the top section so as to form a ridge around the base of the top section upon which the snuffer cap may rest. The outer circumference of the bottom section is larger than the outer circumference of the middle section so as to form a ridge around the base of the middle section that hides the protruding lip of the decanter body. The fragrance diffuser kit of the invention may also comprise a set of instruction for using the kit.

The invention further provides a method of introducing a fragrance into a home environment. As a first step, a fragrance diffuser kit as described above may be selected. The fragrance composition contained in the bottle of the fragrance refill set may then be poured into the decanter body through the top opening of the wick holder, preferably using a funnel supplied with the fragrance refill set. The wick may then be inserted into the wick holder so that a bottom portion of the wick extends into the decanter body to be immersed by the fragrance composition contained therein, and a top portion extends above the top of the wick holder a distance sufficient to allow fragrance composition absorbed in the wick to evaporate therefrom into the surrounding environment. The wick holder may then be covered with the decorative vented lid. In one embodiment, the top portion of the wick may be covered with the snuffer cap to stop the evaporation of the fragrance composition before covering the wick holder with the decorative vented lid.

In another embodiment, the wick may be removed from the wick holder and any remaining liquid fragrance composition may be emptied from the decanter body. A second fragrance refill set containing a bottle of a second volatile liquid fragrance composition and a second rod-shaped wick may then be selected. The second liquid fragrance composition may be poured into the decanter body through the top opening of the wick holder, and the second rod-shaped wick may be inserted into the wick holder so that a bottom portion of the wick is immersed in the second fragrance composition contained in the decanter body and a top portion extends above the wick holder as previously described. The wick holder and the top portion of the second wick may then be covered with the decorative vented lid.

DETAILED DESCRIPTION OF THE INVENTION

Specific embodiments of the invention will now be described with reference to the drawings. The same reference numbers are used in different drawings to refer to the same element.

Figure 1:
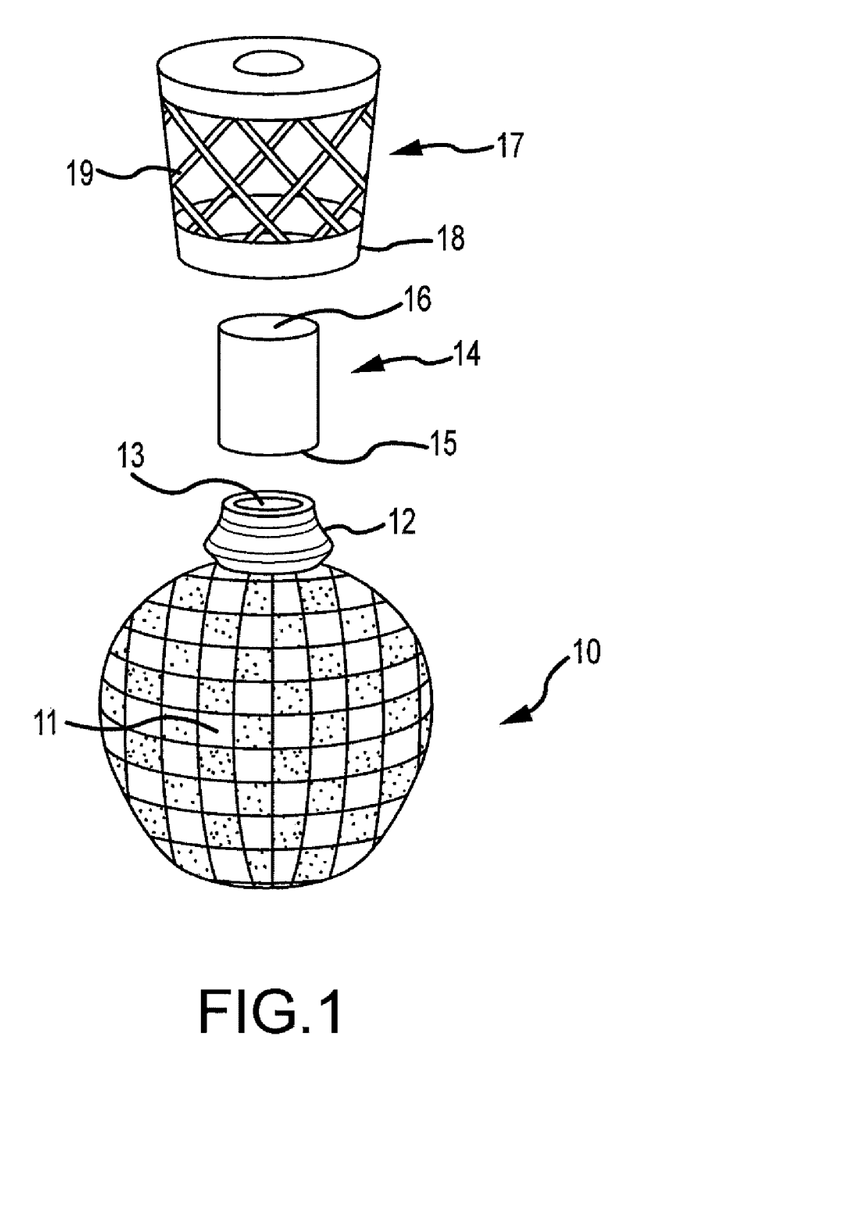
FIG. 1 illustrates a perspective view of an exemplary decanter, snuffer cap and vented lid contained in the fragrance diffuser kit of the present invention.

FIG. 1 illustrates exemplary embodiments of the decanter, snuffer cap and decorative vented lid elements of a fragrance diffuser kit according to the present invention. In one embodiment, decanter 10 may comprise a distinctive decorative hollow body 11 and a wick holder 12 having an annular top opening 13 that communicates with the interior of decanter body 11. As will be described in more detail below, the hollow interior of decanter body 11 is adapted to be filled with a volatile liquid fragrance composition through top opening 13, and wick holder 12 is adapted to removably hold a wick so that a bottom portion of the wick is immersed in the liquid fragrance composition in decanter body 11 and a top portion extends above the wick holder to be exposed to the atmosphere. Decanter body 11 is preferably manufactured from a durable inert material, such as glass or ceramic, that can be fashioned into a relatively permanent piece of décor similar to a vase, liquor decanter, ornamental bottle, etc. Decanter body 11 may take a wide variety of shapes, sizes and exterior surfaces.

Snuffer cap 14 may comprise a hollow cylinder having an open end 15 and a closed end 16. As described in more detail below, open end 15 of snuffer cap 14 is adapted to removably engage with wick holder 12 so as to cover the exposed top portion of a wick that has been positioned within wick holder 12. Snuffer cap 14 is preferably manufactured from a high gloss metallic material which matches the color and appearance of wick holder 12 and complements the design of decorative body 11 of decanter 10.

Decorative vented lid 17 may comprise a circular base 18 and an open body 19. Base 18 is configured to fit over the base of wick holder 12 and rest on the top of decanter body 11. Open body 19 of lid 17 may comprise a wide variety of ornamental designs that provide vents, openings or spaces through which fragrance composition vapors may pass, yet open body 19 is substantial enough to effectively hide wick holder 12 and any wick held thereby, as well as snuffer cap 14 if present. For example, decorative vented lid 17 may be made of a shiny metallic material and take the shape of a crown having decorative cutout sides, or a cylinder with an open lattice framework, as shown in FIG. 1.

Figure 2:
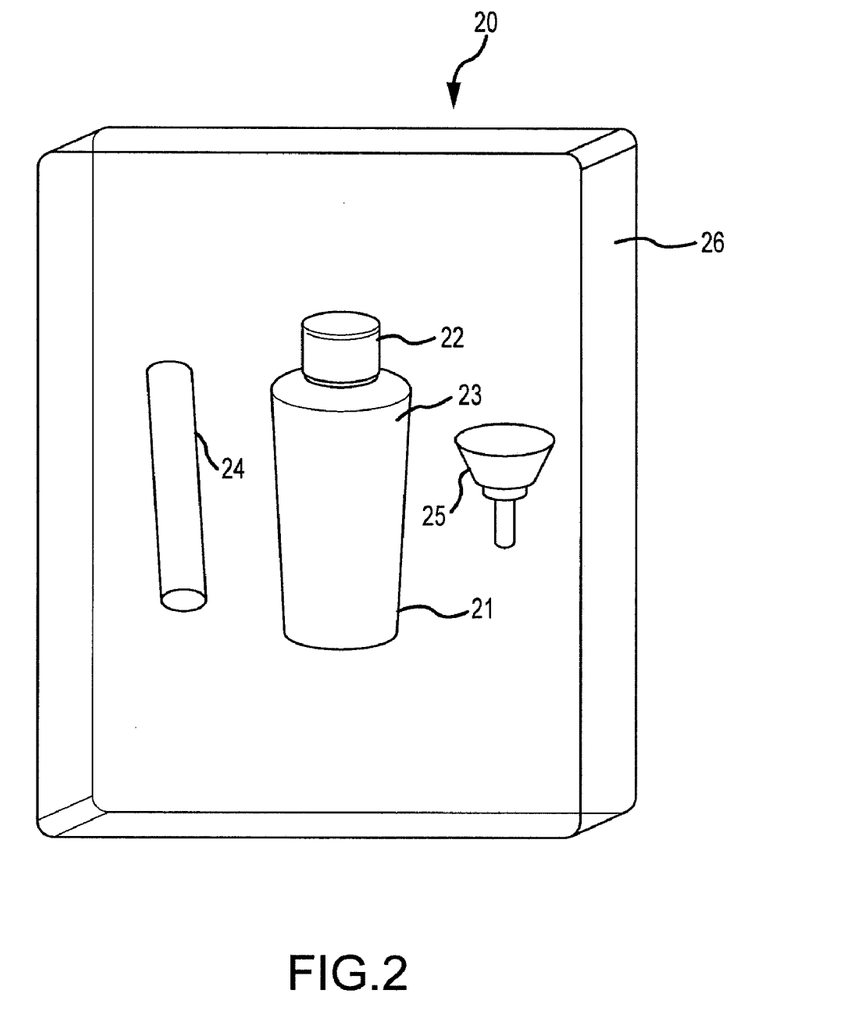
FIG. 2 illustrates a perspective view of an exemplary packaged fragrance refill set contained in the fragrance diffuser kit of the present invention.

FIG. 2 illustrates an exemplary fragrance refill set contained in the fragrance diffuser kit of the invention. Fragrance refill set 20 may comprise a bottle 21 with cap 22 which contains liquid volatile fragrance composition 23. Fragrance refill set 20 may also include a rod-shaped absorbent wick 24 and a funnel 25. All of the elements of fragrance refill set 20 may be conveniently packaged in packaging 26, thereby making refill set 20 suitable for retail display and separate sale, preferably in the cosmetics area of a store where fine fragrances are sold.

Fragrance composition 23 is preferably a high quality, complex home fragrance composition made from natural essential oils and/or other natural ingredients, such as, for example, one of the luxury home fragrance compositions sold under the Claire Burke® trademark. As an example of a Claire Burke® fragrance composition contemplated as useful in the invention, mention may be made of a green tea ginger and pear composition, which includes Italian bergamot, ginger zest and white pear nectar with citrus musk accord. Another example of a suitable Claire Burke® fragrance is a lily jasmine and musk composition that contains top notes of wild greens, summer melon and a hint of raspberry, with heart notes of sunflower, rose, veliver, white muguet, jasmine and cyclamen, in a base blend of ozone infused musks with white woods. Another example of a suitable Claire Burke® fragrance is a lime verbena and bay composition containing top notes of bergamot, verbena, lime and mandarin wrapped in herbaceous greens, with hints of bay, thyme and basil, and nuances of white lily, rose and jasmine, white musk and soft woods completing the scent. A still further example of a suitable Claire Burke® fragrance includes a lavender vanilla and sandalwood composition comprising a herbaceous blend of French lavender, sheer eucalyptus, Roman chamomile and a herbal bouquet sweetened by Tahitian vanilla, combined with sandalwood, other precious woods and floral musks.

Wick 24 is preferably rod-shaped and is adapted to be inserted into wick holder 12 and extend into decanter body 11, as previously described. Wick 24 may be made from any suitable absorbent wicking material such as cotton, cellulose, or another material that is capable of absorbing the liquid fragrance composition 23 and transferring it by capillary action to a portion of wick 24 where it is exposed to the ambient environment and can evaporate into the atmosphere. The wicking material may be encased in paper or other support material to give wick 24 enough structural strength to be handled, as well as to be inserted into and removed from wick holder 12, without damage.

Funnel 25 may be conveniently included in fragrance refill set 20 to facilitate the pouring of fragrance composition 23 from bottle 21 into top opening 13 of decanter 10. Funnel 25 is configured to fit into top opening 13 and may be made of any suitable material. Although funnel 25 is designed to be disposable, it is preferably made to be attractive in appearance and relatively substantial so as to match the high quality of the remaining elements of the fragrance diffuser kit.

Figure 3:
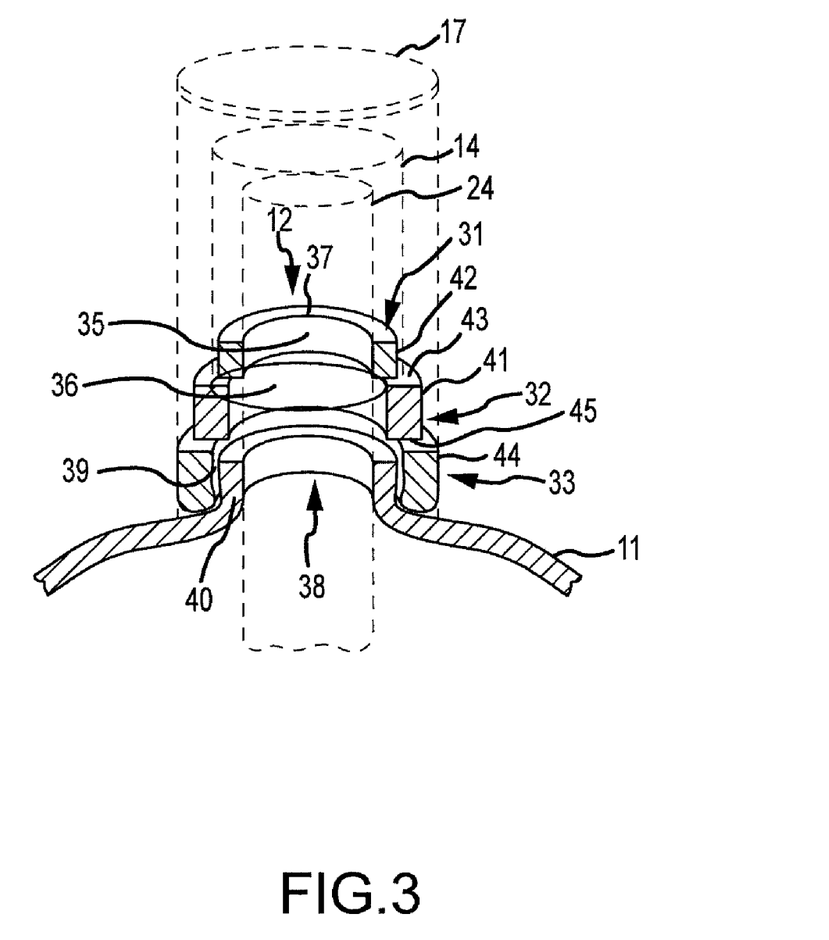
FIG. 3 illustrates a cross-section view of one embodiment of an exemplary wick holder contemplated by the invention.

Wick holder 12 is designed to be a decorative addition to decanter 10, as well as provide a means for functionally connecting together the various elements of the fragrance diffuser kit of the present invention. FIG. 3 illustrates one embodiment of wick holder 12 that comprises three vertically disposed, concentric cylindrical sections: a top cylindrical section 31, a middle cylindrical section 32 and a bottom cylindrical section 33. Inner circumference 35 of top section 31 and inner circumference 36 of middle section 32 define a closed hollow passageway that connects wick holder top opening 37 with decanter top opening 38. Wick 24 may be inserted into wick holder top opening 37 so as to extend through decanter top opening 38 into the interior of decanter body 11. The outer circumference of wick 24 is substantially equal to inner circumference 35 of wick holder 12 so as to provide a snug fit. This snug fit is tight enough to hold wick 24 in position, but is not so tight as to prevent the removal of wick 24 from wick holder 12 when desired. Inner circumference 39 of bottom section 33 engages vertically protruding lip 40 around decanter top opening 38 so as to fixedly secure wick holder 12 to decanter body 11. For example, bottom section 33 may be crimped or glued around protruding lip 40 to secure wick holder 12 to decanter body 11.

Outer circumference 41 of middle section 32 is larger than outer circumference 42 of top section 31 so as to form ridge 43 around the base of top section 31. The inner circumference of opening 15 (FIG. 1) in snuffer cap 14 is substantially equal to the outer circumference 42 of top section 31, thereby providing a snug fit when snuffer cap 14 is placed over top section 31 and opening 15 is rested on ridge 43 of wick holder 12. This snug fit is sufficient to hold snuffer cap 14 in place on wick holder 12, but is not so tight as to prevent the removal of snuffer cap 14 when desired. The top portion of wick 24 is configured to be completely covered by snuffer cap 14 when in place on wick holder 12. Outer circumference 44 of bottom section 33 is larger than outer circumference 41 of middle section 32 thereby providing ridge 45 that covers protruding lip 40, thereby hiding it from view. However, outer circumference 44 of bottom section 33 is smaller than the opening in base 18 (FIG. 1) of vented lid 17 so that vented lid 17 may be placed over wick holder 12 with base 18 of vented lid 17 resting on body 11 of decanter 10.

Preferred wick holder 12 of the invention allows a wide variety of decanter body styles, shapes, sizes and decorative surfaces to be offered for inclusion in diffuser kits of the invention. A decanter body need only be manufactured with a suitable protruding lip 40 for installing wick holder 12 and the decanter body will then be compatible with the remaining elements of the fragrance diffuser kit.

The fragrance diffuser kit of the present invention may further contain a set of instructions describing a method for using the kit. One embodiment of a method according to the invention is illustrated in FIGS. 4-7.

Figure 4:
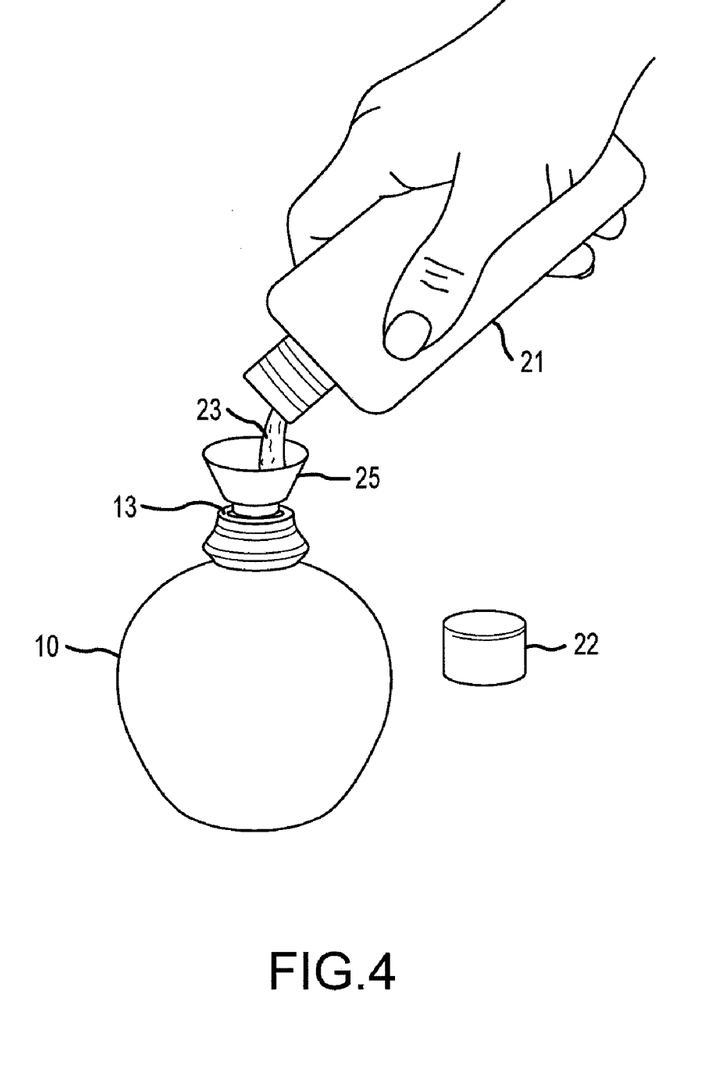
FIG. 4 illustrates the pouring step according to the method of the invention.
Figure 5:
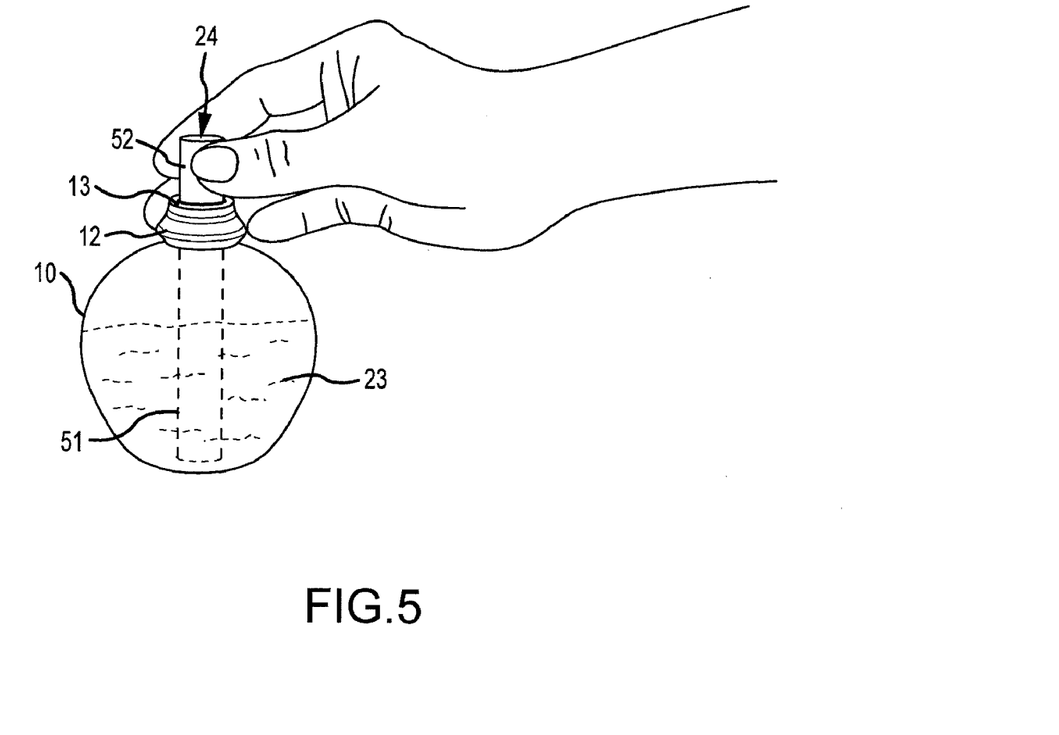
FIG. 5 illustrates the insertion of a wick into the wick holder of a decanter according to the method of the invention.
Figure 6:
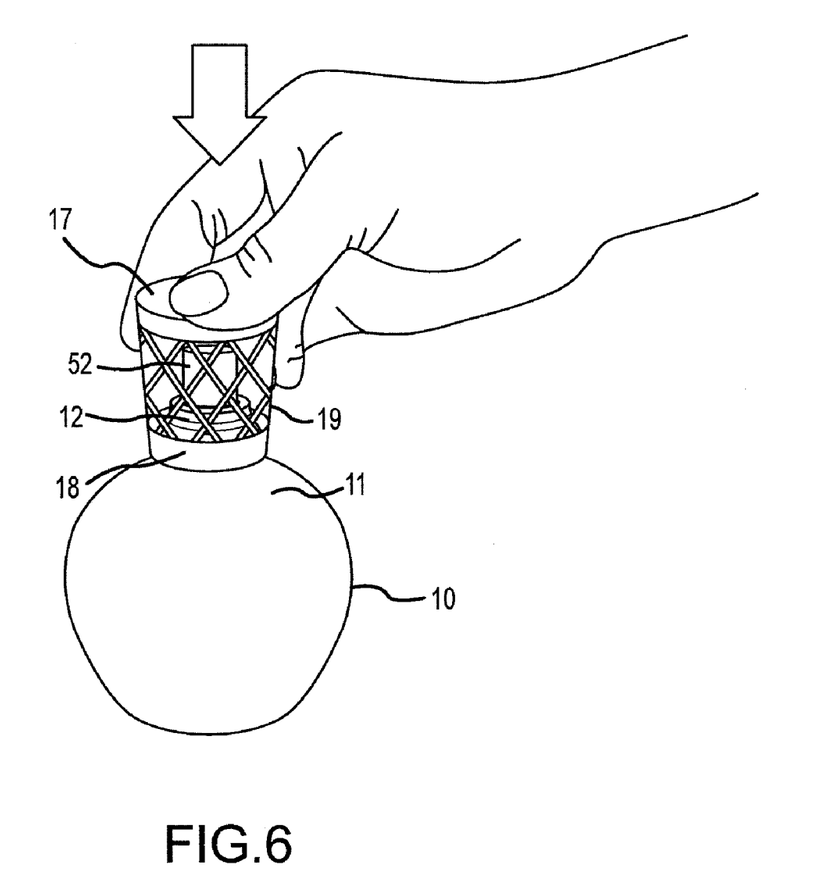
FIG. 6 illustrates the covering of the wick holder and top portion of the wick with a vented lid in accordance with the method of the invention.
Figure 7:
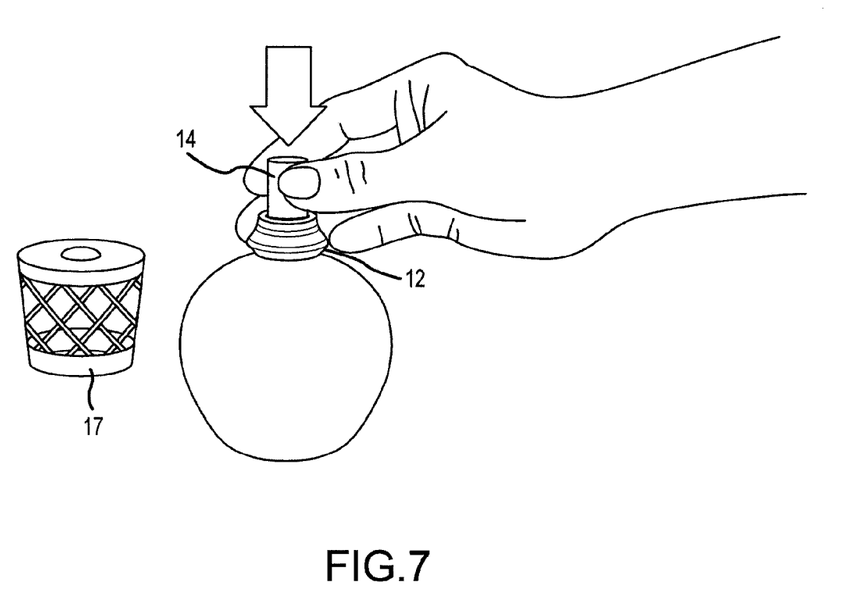
FIG. 7 illustrates the covering of the top portion of the wick with a snuffer cap in accordance with the method of the invention.

Referring now to FIG. 4, after selecting the desired fragrance diffuser kit, cap 22 may be removed from bottle 21 contained in fragrance refill set 20, and liquid fragrance composition 23 may be poured from bottle 21 into decanter 10, preferably using funnel 25 inserted into top opening 13. As shown in FIG. 5, wick 24 may be inserted into wick holder 12 through top opening 13 so that bottom portion 51 is immersed in fragrance composition 23 contained in decanter 10 and top portion 52 extends above wick holder 12. Top portion 52 has sufficient exposed length that fragrance composition 23 that has absorbed into wick 24 in bottom portion 51, and has moved by capillary action to top portion 52, may evaporate therefrom into the surrounding environment. Referring now to FIG. 6, decorative vented lid 17 may be placed over wick holder 12 with base 18 resting on body 11 of decanter 10 so as to cover wick holder 12, as well as top portion 52 of wick 14 held therein. As shown in FIG. 7, top portion 52 (not shown) of wick 24 may be covered by installing snuffer cap 14 on wick holder 12 whenever it is desired to stop the evaporation of the fragrance composition into the surrounding environment. Decorative vented lid 17 may be removed to accommodate the installation of snuffer cap 14 and then replaced to cover wick holder 12, as well as snuffer cap 14 installed thereon.

The invention has now been described in detail for purposes of clarity of understanding. However, it is understood that certain changes and modifications may be made. For example, various elements of the fragrance diffuser kit may be interchanged. For example, the decorative vented lid of one kit may be replaced with a different decorative vented lid from another kit, a decorative decanter from one kit may be replaced with a different decorative decanter from another kit, and so forth. Therefore, the scope and content of the invention are not limited by the foregoing description. Rather, the scope and content are to be defined by the following claims.

What is claimed is:

1. A fragrance diffuser kit comprising:

a decanter, a fragrance refill set, a removable snuffer cap and a removable decorative vented lid;

wherein said decanter has a distinctive decorative hollow body with an annular top opening and a wick holder fixedly secured to the hollow body, the wick holder having an annular top opening that communicates with the top opening of the decanter body;

wherein said fragrance refill set contains a bottle of a volatile liquid fragrance composition for filling the decanter body and a rod-shaped absorbent wick adapted to be removably held by the wick holder of the decanter so that a bottom portion of the wick is immersed in fragrance composition contained in the decanter body and a top portion extends above the wick holder a distance sufficient to allow fragrance composition absorbed in the wick to evaporate therefrom;

wherein the removable snuffer cap is adapted to fit over the top portion of the wick to prevent evaporation of fragrance composition therefrom when desired;

wherein the removable decorative vented lid is adapted to cover the wick holder, the top portion of the wick and the snuffer cap, when present; and wherein the decanter body has a protruding lip around the circumference of the top opening, and the wick holder comprises a top cylindrical section, a middle cylindrical section and a bottom cylindrical section, said sections being vertically disposed in a concentric arrangement whereby the inner circumferences of the top and middle sections define a closed hollow passageway connecting the top opening of the decanter body with the top opening of the wick holder, and the inner circumference of the bottom section engages the protruding lip of the decanter body to secure the wick holder to the decanter body, and whereby the outer circumference of the middle section is larger than the outer circumference of the top section so as to form a ridge around the base of the top section upon which the base of the snuffer cap rests, and whereby the outer circumference of the bottom section is larger than the outer circumference of the middle section so as to hide the protruding lip of the decanter body.

2. A fragrance diffuser kit as in claim 1 wherein the fragrance refill set further comprises a funnel to facilitate the filling of the body of the decanter with the liquid fragrance material.

3. A fragrance diffuser kit as in claim 1 wherein the fragrance refill set is packaged and sold separately from the decanter body, snuffer cap and vented lid.

4. A fragrance diffuser kit as in claim 1 further comprising a set of instructions describing a method for using the kit.

5. A fragrance diffuser kit as in claim 1 wherein the liquid fragrance composition is made from natural essential oils and/or other natural ingredients.

6. A method for introducing a fragrance into a home environment, said method comprising the steps of:

selecting a fragrance diffuser kit comprising a decanter, a fragrance refill set, a removable snuffer cap, and a removable decorative vented lid, wherein the decanter has a distinctive decorative hollow body with an annular top opening and a wick holder fixedly secured to the hollow body, wherein the wick holder has an annular top opening that communicates with the top opening of the decanter body, wherein the fragrance refill set contains at least a bottle of a volatile liquid fragrance composition and a rod-shaped wick;

pouring the liquid fragrance composition from the bottle into the decanter body through the top opening of the wick holder;

inserting the wick into the wick holder so that a bottom portion of the wick is immersed in the fragrance composition contained in the decanter body and a top portion extends above the wick holder a distance sufficient to allow fragrance composition absorbed in the wick to evaporate therefrom into the surrounding environment; and covering the wick holder with the decorative vented lid.

7. A method as in claim 6 further comprising:

covering the top portion of the wick with the snuffer cap to stop the evaporation of the fragrance composition into the surrounding environment before covering the wick holder with the decorative vented lid.

8. A method as in claim 6 further comprising:

removing the wick from the wick holder;

emptying any remaining liquid fragrance composition from the decanter body;

selecting a second fragrance refill set containing a bottle of a second volatile liquid fragrance composition and a second rod-shaped wick;

pouring the second liquid fragrance composition into the decanter body through the top opening of the wick holder;

inserting the second rod-shaped wick into the wick holder so that a bottom portion of the wick is immersed in the second fragrance composition contained in the decanter body and a top portion extends above the wick holder a distance sufficient to allow fragrance composition absorbed in the wick to evaporate therefrom into the surrounding environment; and covering the wick holder with the decorative vented lid.

9. A method as in claim 8 wherein the second fragrance composition is different from the first fragrance composition.

* * * * *